US005665388A

United States Patent [19]
Phykitt

[11] Patent Number: 5,665,388
[45] Date of Patent: Sep. 9, 1997

[54] METHOD FOR PREPARATION OF AN ALKALINE AND ASPIRIN COMBINATION COMPOUND

[75] Inventor: Howard P. Phykitt, Wilson, N.C.

[73] Assignee: Health Corporation, Rocky Mount, N.C.

[21] Appl. No.: 555,900

[22] Filed: Nov. 13, 1995

[51] Int. Cl.$^6$ ................................................ A61K 9/20
[52] U.S. Cl. ................................. 424/464; 424/489
[58] Field of Search ........................... 424/44, 489, 464, 424/43; 544/343

[56] References Cited

U.S. PATENT DOCUMENTS

| | | | |
|---|---|---|---|
| 2,985,562 | 5/1961 | Millard et al. | 67/82 |
| 3,105,792 | 10/1963 | White | 167/57 |
| 3,773,922 | 11/1973 | Gergely | 424/44 |
| 4,093,710 | 6/1978 | Sass et al. | 424/44 |
| 4,515,949 | 5/1985 | Santroch et al. | 544/343 |

FOREIGN PATENT DOCUMENTS 1328591  8/1973  France .

*Primary Examiner*—Thurman K. Page
*Assistant Examiner*—William E. Benston, Jr.
*Attorney, Agent, or Firm*—James Ray & Assoc.

[57] ABSTRACT

A method of manufacturing a stabilized, essentially sodium free, granular aspirin compound mixed with a granular potassium bicarbonate compound comprising the steps of determining a desirable dose size of such aspirin compound which is to be packaged. Weighing out an amount of granular aspirin based on the dose size determined. Placing an amount of such granular potassium bicarbonate compound into a container which is uniformly distributed over a bottom surface of such container to a predetermined depth. Placing such container into a heat treating apparatus. Heat treating the granular potassium bicarbonate compound at a temperature which is at least sufficient to convert an outer surface layer of such granular potassium bicarbonate compound to potassium carbonate and for a time which is at least sufficient to ensure that essentially all of such outer surface layer of the granular potassium bicarbonate compound is converted to such potassium carbonate. Weighing out an amount of such heat treated granular potassium bicarbonate compound based on the dose size determined. Placing the granular aspirin into a package and, thereafter, placing such heat treated granular potassium bicarbonate compound into such package thereby forming the stabilized, essentially sodium free, granular aspirin compound mixed with a granular potassium bicarbonate compound.

20 Claims, No Drawings

METHOD FOR PREPARATION OF AN ALKALINE AND ASPIRIN COMBINATION COMPOUND

CROSS REFERENCE TO RELATED APPLICATION

This application is closely related to my co-pending patent application titled, "ALKALINE AND ASPIRIN COMBINATION COMPOUND" which is being filed concurrently herewith. The teachings of this co-pending patent application are incorporated herein by reference thereto.

FIELD OF THE INVENTION

The present invention relates, in general, to aspirin compounds and, more particularly, this invention relates to a method of manufacturing a stabilized, essentially sodium free, granular aspirin compound mixed with a granular potassium bicarbonate compound that can be more widely used in relatively large doses in the treatment of arthritis and taken in relatively small doses to substantially minimize the incidence of heart attacks without the harmful side-effects normally associated with relatively large doses of aspirin.

BACKGROUND OF THE INVENTION

Aspirin is a drug that has been around for 100 years. Nevertheless, The National Institute of Health is currently sponsoring at least 35 studies designed to probe aspirin's therapeutic role in conditions as diverse as hearing loss and allergies. It is touted as an anti-heart attack and anti-stroke medicine and is considered the number one medication for every type of arthritis.

The "humble" aspirin still remains the gold standard for pain relievers as well as the cheapest. For example, you can pay more than 20 times the cost of aspirin for an anti-inflammatory agent, which requires a prescription, and still not experience better pain relief. No drug in the world outsells aspirin and yet all the drug companies are still searching for a "better" aspirin.

In many cases, aspirin is the drug of choice and the mainstay of arthritis therapy. The common dosages of aspirin (325 mg or 500 mg), however, only provide relief of the symptom of arthritis (pain). In order to achieve effective control of inflammation, the cause of arthritis, daily dosages of greater than 5,000 mg are needed. At these higher dose levels the rate of success is over 70%. However, the success rate falls off dramatically and with 2500 mg. for example, it is less than 10%. Thus, the cause of failure or the lack of success with aspirin therapy is the use of inadequate dosages.

At the present time there is no satisfactory aspirin product available that may be used in the relatively large dosages that are required for anti-inflammatory activity. In addition, in many cases, pain and inflammation may not be relieved immediately, and treatment is a cumulative effect to obtain a "therapeutic level".

Unfortunately, aspirin exhibits a number of undesirable side effects. The most commonly experienced side effects are nausea, gastric upset (heartburn) and pain. At low analgesic dose levels these side effects will generally occur in about 2–10% of adult users of aspirin. With higher anti-inflammatory dosages the incidence of these undesirable side effects generally rises to about 25%.

The side effects are topical, as aspirin is an insoluble drug and it's undissolved particles tend to adhere to the stomach mucosa, causing irritation, inflammation and injury. The topical nature of these detrimental side effects has been established by gastroscopy and autopsies. Erosion, for example, around undissolved particles of aspirin in the stomach have been photographed. Because aspirin is a direct irritant to the gastrointestinal mucosa it's effects are both cumulative and persistent.

Topical side effects do not occur, however, when aspirin is administered in solution form. While all users of aspirin could benefit greatly from the advantages of it's soluble form, older patients are in particular need of such a soluble aspirin product because arthritis is a dreaded disease of old age. The elderly, as a group, are the largest users of aspirin and, at the same time, the most vulnerable to it's acute side effects. The incidence of these detrimental side effects is about 25% among geriatric patients.

Owing to reduced stomach motility and increased emptying time which occur with aging, insoluble aspirin particles remain in contact with the stomach mucosa much longer in the elderly, thereby intensifying the undesirable side effects. In addition, there are approximately 15 million people, in the U.S., who experience some degree of difficulty in swallowing tablets and other solid medications. Older people, once again, are effected as esophagus muscles weaken with age and make swallowing much more difficult.

As is generally well known, there are some soluble aspirin products that are available commercially in the U.S., and Europe. Unfortunately, they all suffer from one or more shortcomings which have prevented their universal acceptance, especially in the United States. For example, the only soluble product which is commercially available in the United States, "Alka Seltzer", contains 567 mg of sodium per 325 mg of aspirin (1,750 mg per 1,000 mg of aspirin).

In order to provide anti-inflammatory activity with Alka Seltzer it would require daily ingestion of more than 8,000 mg of sodium. This amount of sodium makes it totally unacceptable for regular aspirin therapy. Not only is this sodium level extremely high, for the population in general, but it can not be tolerated by many of the elderly arthritic who are also on a restricted sodium diet.

Other products available in Europe either also contain sodium, dissolve incompletely or could not win FDA approval in the U.S. for some reason. Despite their shortcomings, however, these products still capture a large share of the market for aspirin products from Europe to Mexico.

Numerous attempts to produce a soluble aspirin product, in the past, have included salts of lithium, sodium, calcium and magnesium. None of these soluble aspirin salt products were proven to be totally satisfactory. It is generally well recognized in the art that these particular salts are not only unstable, but also produce a number of undesirable side effects.

Even though potassium possesses many properties that would make it an ideal compound for this purpose, potassium aspirin has never been developed as a satisfactory commercial product. The primary reason is that the salts formed with potassium form bitter, unpalatable solutions. Thus, potassium acetylsalicylate (potassium aspirin) would be an ideal aspirin replacement if it could be made palatable.

SUMMARY OF THE INVENTION

The instant invention provides a method of manufacturing a stabilized, essentially sodium free, granular aspirin compound mixed with a granular potassium bicarbonate compound. Such method includes the steps of determining a desirable dose size for such stabilized, essentially sodium free, granular aspirin compound to be mixed with the granular potassium bicarbonate compound. Thereafter, weighing out a predetermined amount of granular aspirin, having a predetermined particle size, based on such dose size determined. A predetermined amount of such granular potassium bicarbonate compound is placed into a container and such potassium bicarbonate compound is then substantially uniformly distributed over a bottom surface of such container to a predetermined depth. Such container, containing such granular potassium bicarbonate compound therein, is thereafter placed into a heat treating apparatus. Heat treating of such predetermined amount of the granular potassium bicarbonate compound is carried out at a predetermined temperature which is at least sufficient to convert an outer surface layer of this granular potassium bicarbonate compound to potassium carbonate and for a predetermined time which is at least sufficient to ensure that essentially all of such outer surface layer of the granular potassium bicarbonate compound is converted to such potassium carbonate. Then, weighing out a predetermined amount of such granular potassium bicarbonate compound after completion of such heat treating based on the predetermined dose size determined. Such predetermined amount of granular aspirin is then placed into a suitable package and such predetermined amount of the granular potassium bicarbonate compound is added to such package thereby forming the stabilized, essentially sodium free, granular aspirin compound mixed with such granular potassium bicarbonate compound.

OBJECTS OF THE INVENTION

It is, therefore, one of the primary objects of the present invention to provide a method of manufacturing a stabilized, essentially sodium free, granular aspirin compound mixed with a granular potassium bicarbonate compound which will enable such aspirin compound to be more widely used in the aspirin therapy treatment of arthritis and other ailments for which aspirin is normally used.

Another object of the present invention is to provide a method of manufacturing a stabilized, essentially sodium free, granular aspirin compound mixed with a granular potassium bicarbonate compound which is relatively stable over an extended shelf life of the product.

Still another object of the present invention is to provide a method of manufacturing a stabilized, essentially sodium free, granular aspirin compound mixed with a granular potassium bicarbonate compound which ensures that the outer surface layer of the granules of potassium bicarbonate are completely converted to potassium carbonate.

Yet another object of the present invention is to provide a method of manufacturing a stabilized, essentially sodium free, granular aspirin compound mixed with a granular potassium bicarbonate compound that can be dissolved in a minimum amount of water, in a relatively short time, with stirring by hand with a spoon.

An additional object of the present invention is to provide a method of manufacturing a stabilized, essentially sodium free, granular aspirin compound mixed with a granular potassium bicarbonate compound which will not irritate the gastric system.

It is still another object of the present invention to provide a method for the manufacture of a stabilized, essentially sodium free, granular aspirin compound mixed With a granular potassium bicarbonate compound that is relatively simple and inexpensive.

Still another object of the present invention is to provide a method for the manufacture of a stabilized, essentially sodium free, granular aspirin compound mixed with a granular potassium bicarbonate compound which is substantially totally soluble in water and thereby form potassium acetylsalicylate when dissolved.

A further object of the present invention is to provide a method for the manufacture of a stabilized, essentially sodium free, granular aspirin compound mixed with a granular potassium bicarbonate compound which does not contain a sodium compound.

An additional object of the present invention is to provide a method for the manufacture of a stabilized, essentially sodium free, granular aspirin compound mixed with a granular potassium bicarbonate compound which can act as an antacid.

Still yet another object of the present invention is to provide a method for the manufacture of a stabilized, essentially sodium free, granular aspirin compound mixed with a granular potassium bicarbonate compound which has the potential to reduce the incidence of heart attack.

Yet still another object of the present invention is to provide a method for the manufacture of a stabilized, essentially sodium free, granular aspirin compound mixed with a granular potassium bicarbonate compound which has the potential to reduce the incidence of strokes.

A still further object of the present invention is to provide a method for the manufacture of a stabilized, essentially sodium free, granular aspirin compound mixed with a granular potassium bicarbonate compound which has the potential to substantially prevent osteoporosis.

In addition to the several objects and advantages of the present invention which have been described in detail above, various other objects and advantages of the present invention will become readily apparent to those persons skilled in aspirin production from the following more detailed description of such invention.

BRIEF DESCRIPTION OF A PRESENTLY PREFERRED AND VARIOUS ALTERNATIVE EMBODIMENTS OF THE INVENTION

The present invention provides a method of manufacturing a stabilized, essentially sodium free, granular aspirin compound mixed with a granular potassium bicarbonate compound. The method, according to the invention, includes the steps of first determining a desirable dose size for the stabilized, essentially sodium free, granular aspirin compound mixed with the granular potassium bicarbonate compound which is to be packaged.

A predetermined amount of granular aspirin, having a predetermined particle size, based on the dose size determined in the previous step is weighed out. Although the present invention is not limited thereto, the dose size will usually be between about 325.0 mg and about 1,000.0 mg. In the presently preferred embodiment of the invention, the predetermined particle size of the granular aspirin is USP −60 mesh or smaller.

A predetermined amount of the granular potassium bicarbonate compound is placed into a suitable container. The potassium bicarbonate compound is then substantially uniformly distributed over a bottom surface of the container to a predetermined depth. According to the presently preferred embodiment of the invention, the depth of such potassium bicarbonate will generally be between about one-quarter inch and about one and one-half inches.

It is presently preferred that the granular potassium bicarbonate compound is a food grade Flow K, a registered Trademark of Church and Dwight, and the predetermined amount of such granular potassium bicarbonate compound will generally be in the range of between about 250.0 mg and about 3,000.0 mg. The presently preferred range being between about 400.0 mg and about 1,210.0 mg.

The container containing the granular potassium bicarbonate compound therein is then placed into a heat treating apparatus. The predetermined amount of the granular potassium bicarbonate compound is then heat treated at a predetermined temperature which is at least sufficient to convert an outer surface layer of the granular potassium bicarbonate compound to potassium carbonate and for a predetermined time which is at least sufficient to ensure that essentially all of the outer surface layer of the granular potassium bicarbonate compound is converted to potassium carbonate.

In the invented method for manufacturing a stabilized, essentially sodium free, granular aspirin compound mixed with a granular potassium bicarbonate compound it has been found that the predetermined temperature will generally be in a range of between about 60 degrees C. and about 150 degrees C. It is presently preferred that the predetermined temperature be in a range of between about 90 degrees C. and about 120 degrees C.

Additionally, according to the method of manufacturing a stabilized, essentially sodium free, granular aspirin compound mixed with a granular potassium bicarbonate compound, the predetermined time is generally in a range of between about 5.0 hours and about 30.0 hours. It is presently preferred that this time be in a range of between about 10.0 hours and about 21.0 hours.

A predetermined amount of the granular potassium bicarbonate compound, after completion of the heat treating in the previous step, is weighed out based on the predetermined dose size that had determined previously.

Next, the predetermined amount of the granular aspirin, weighed out in the first step is placed into a package and thereafter, the predetermined amount of the granular potassium bicarbonate compound that was weighed out previously is placed into the package thereby forming the stabilized, essentially sodium free, granular aspirin compound mixed with the granular potassium bicarbonate compound.

The method of manufacturing a stabilized, essentially sodium free, granular aspirin compound mixed with a granular potassium bicarbonate compound, according to a presently preferred alternative embodiment, includes the additional steps of selecting a sweetening agent to be incorporated into the stabilized, essentially sodium free, granular aspirin compound mixed with a granular potassium bicarbonate and weighing out a predetermined amount of this sweetening agent.

In the presently preferred alternative method of manufacturing a stabilized, essentially sodium free, granular aspirin compound mixed with a granular potassium bicarbonate compound this predetermined amount of the sweetening agent will generally be in a range of between about 1,135.0 mg and about 5,000.0 mg. In the presently preferred embodiment of the method the sweetening agent is selected from a group consisting of sucrose, fructose, saccharin, aspartame, dextrose and various mixtures thereof. The presently preferred sweetening agent is sucrose.

The method of manufacturing a stabilized, essentially sodium free, granular aspirin compound mixed with a granular potassium bicarbonate compound, may also include the additional step of selecting a flavoring agent to be incorporated into the stabilized, essentially sodium free, granular aspirin compound mixed with a granular potassium bicarbonate and weighing out a predetermined amount of the flavoring agent.

In this alternative method of manufacturing a stabilized, essentially sodium free, granular aspirin compound mixed with a granular potassium bicarbonate compound the predetermined amount of the flavoring agent is generally in a range of between about 10.0 mg and about 30.0 mg. The flavoring compound is selected from a group consisting of fruit flavors. Such fruit flavors being selected from the group consisting of orange, lemon, lime, cherry and various mixtures thereof.

The method of manufacturing a stabilized, essentially sodium free, granular aspirin compound mixed with a granular potassium bicarbonate compound, may also include the additional step of selecting an acidic compound to be incorporated into the stabilized, essentially sodium free, granular aspirin compound mixed with a granular potassium bicarbonate and weighing out a predetermined amount of the acidic compound. The predetermined amount of such acidic compound will generally be in the range of between about 15.0 mg and about 1,000.0 mg. These acidic compounds are selected from the group consisting of citric acid, ascorbic acid, maleic acid, tartaric acid and various mixtures thereof. The most preferred acidic compound is citric acid.

In the method of manufacturing a stabilized, essentially sodium free, granular aspirin compound mixed with a granular potassium bicarbonate compound, each of the predetermined amounts of the previously weighed granular aspirin, previously weighed sweetening agent, previously weighed flavoring agent, and the previously weighed acidic compound are placed into a mixing vessel. Then, intimate mixing of the predetermined amount of the granular aspirin and the predetermined amount of the sweetening agent and the predetermined amount of the flavoring agent and the predetermined amount of the acidic compound is carried out.

In this alternative method of manufacturing a stabilized, essentially sodium free, granular aspirin compound mixed with a granular potassium bicarbonate compound the predetermined amounts of the previously weighed granular aspirin, previously weighed sweetening agent, previously weighed flavoring agent, and the previously weighed acidic compound can be added and mixed in the mixing vessel in any order.

In the method of manufacturing a stabilized, essentially sodium free, granular aspirin compound mixed with a granular potassium bicarbonate compound the molar amount of granular potassium bicarbonate compound used is greater than the molar amount required to neutralize the granular aspirin.

It can be seen from the above description that the present invention provides a method for the preparation of a water soluble potassium aspirin product developed to meet the special needs of arthritics who suffer from severe arthritis, requiring large doses of anti-inflammatory, analgesic products; aspirin intolerance, due to acute side effects of products now on the market; and the inability to swallow pills or tablets.

While both a presently preferred and various alternative embodiments of the invention have been described in detail above, it should be noted that those persons who are skilled in the drug art can make other adaptations and modifications to the method of manufacturing a stabilized, essentially sodium free, granular aspirin compound mixed with a granular potassium bicarbonate compound without departing either from the spirit of the invention or the scope of the appended claims.

I claim:

1. A method of manufacturing a stabilized, essentially sodium free, granular aspirin compound mixed with a granular potassium bicarbonate compound, said method comprising the steps of:
   (a) determining a desirable dose size of said stabilized, essentially sodium free, granular aspirin compound mixed with said granular potassium bicarbonate compound which is to be packaged;
   (b) weighing out a predetermined amount of granular aspirin, having a predetermined particle size, based on said dose size determined in step (a);
   (c) placing a predetermined amount of said granular potassium bicarbonate compound into a container, said potassium bicarbonate compound being substantially uniformly distributed over a bottom surface of said container to a predetermined depth;
   (d) placing said container, containing said granular potassium bicarbonate compound therein, into a heat treating apparatus;
   (e) heat treating said predetermined amount of said granular potassium bicarbonate compound at a predetermined temperature which is at least sufficient to convert an outer surface layer of said granular potassium bicarbonate compound to potassium carbonate and for a predetermined time which is at least sufficient to ensure that essentially all of said outer surface layer of said granular potassium bicarbonate compound is converted to said potassium carbonate;
   (f) weighing out a predetermined amount of said granular potassium bicarbonate compound, after completion of said heat treating in step (e), based on said predetermined dose size determined in step (a);
   (g) placing said predetermined amount of said granular aspirin, weighed out in step (b), into a package; and
   (h) placing said predetermined amount of said granular potassium bicarbonate compound, weighed out in step (f), into said package thereby forming said stabilized, essentially sodium free, granular aspirin compound mixed with said granular potassium bicarbonate compound.

2. A method of manufacturing a stabilized, essentially sodium free, granular aspirin compound mixed with a granular potassium bicarbonate compound, according to claim 1, wherein said predetermined particle size of said granular aspirin is at least one of USP −60 mesh and smaller.

3. A method of manufacturing a stabilized, essentially sodium free, granular aspirin compound mixed with a granular potassium bicarbonate compound, according to claim 1, wherein said granular potassium bicarbonate compound is food grade Flow K.

4. A method of manufacturing a stabilized, essentially sodium free, granular aspirin compound mixed with a granular potassium bicarbonate compound, according to claim 1, wherein said predetermined temperature is generally in a range of between about 60 degrees C and about 150 degrees C.

5. A method of manufacturing a stabilized, essentially sodium free, granular aspirin compound mixed with a granular potassium bicarbonate compound, according to claim 4, wherein said predetermined temperature is in a range of between about 90 degrees C and about 120 degrees C.

6. A method of manufacturing a stabilized, essentially sodium free, granular aspirin compound mixed with a granular potassium bicarbonate compound, according to claim 4, wherein said predetermined time is generally in a range of between about 5.0 hours and about 30.0 hours.

7. A method of manufacturing a stabilized, essentially sodium free, granular aspirin compound mixed with a granular potassium bicarbonate compound, according to claim 6, wherein said predetermined time is in a range of between about 10.0 hours and about 21.0 hours.

8. A method of manufacturing a stabilized, essentially sodium free, granular aspirin compound mixed with a granular potassium bicarbonate compound, according to claim 1, wherein, prior to step (g), said method includes the additional steps of:
   (i) selecting a sweetening agent to be incorporated into said stabilized, essentially sodium free, granular aspirin compound mixed with a granular potassium bicarbonate and weighing out a predetermined amount of said sweetening agent;
   (j) selecting a flavoring agent to be incorporated into said stabilized, essentially sodium free, granular aspirin compound mixed with a granular potassium bicarbonate and weighing out a predetermined amount of said flavoring agent;
   (k) selecting an acidic compound to be incorporated into said stabilized, essentially sodium free, granular aspirin compound mixed with a granular potassium bicarbonate and weighing out a predetermined amount of said acidic compound;
   (l) placing each of said predetermined amount of said granular aspirin, weighed out in step (b), and said predetermined amount of said sweetening agent, weighed out in step (i), and said predetermined amount of said flavoring agent, weighed out in step (j), and said predetermined amount of said acidic compound, weighed out in step (k), into a mixing vessel; and
   (m) intimately mixing said predetermined amount of said granular aspirin and said predetermined amount of said sweetening agent and said predetermined amount of said flavoring agent and said predetermined amount of said acidic compound, placed into said mixing vessel in step (l).

9. A method of manufacturing a stabilized, essentially sodium free, granular aspirin compound mixed with a granular potassium bicarbonate compound, according to claim 8, wherein said predetermined amount of said granular aspirin is generally in a range of between about 325.0 mg and about 1,000.0 mg.

10. A method of manufacturing a stabilized, essentially sodium free, granular aspirin compound mixed with a granular potassium bicarbonate compound, according to claim 9, wherein said predetermined amount of said sweetening agent is generally in a range of between about 1,135.0 mg and about 5,000.0 mg.

11. A method of manufacturing a stabilized, essentially sodium free, granular aspirin compound mixed with a granular potassium bicarbonate compound, according to claim 10, wherein said predetermined amount of said flavoring agent is generally in a range of between about 10.0 mg and about 30.0 mg.

12. A method of manufacturing a stabilized, essentially sodium free, granular aspirin compound mixed with a granular potassium bicarbonate compound, according to claim 11, wherein said predetermined amount of said acidic compound is generally in a range of between about 15.0 mg and about 1,000.0 mg.

13. A method of manufacturing a stabilized, essentially sodium free, granular aspirin compound mixed with a granular potassium bicarbonate compound, according to claim 9, wherein said predetermined amount of said granular potassium bicarbonate compound is generally in a range of between about 400.0 mg and about 1,210.0 mg.

14. A method of manufacturing a stabilized, essentially sodium free, granular aspirin compound mixed with a granular potassium bicarbonate compound, according to claim 12, wherein said predetermined amount of said granular potassium bicarbonate compound is generally in a range of between about 400.0 mg and about 1,210.0 mg.

15. A method of manufacturing a stabilized, essentially sodium free, granular aspirin compound mixed with a granular potassium bicarbonate compound, according to claim 1, wherein a molar amount of said granular potassium bicarbonate compound is greater than a molar amount required to neutralize said granular aspirin.

16. A method of manufacturing a stabilized, essentially sodium free, granular aspirin compound mixed with a granular potassium bicarbonate compound, according to claim 14, wherein a molar amount of said granular potassium bicarbonate compound is greater than a molar amount required to neutralize said granular aspirin.

17. A method of manufacturing a stabilized, essentially sodium free, granular aspirin compound mixed with a granular potassium bicarbonate compound, according to claim 8, wherein steps (i,j and k) can be performed in any order.

18. A method of manufacturing a stabilized, essentially sodium free, granular aspirin compound mixed with a granular potassium bicarbonate compound, according to claim 17, wherein said sweetening agent is selected from the group consisting of sucrose, fructose, saccharin, aspartame, dextrose and various mixtures thereof.

19. A method of manufacturing a stabilized, essentially sodium free, granular aspirin compound mixed with a granular potassium bicarbonate compound, according to claim 18, wherein said flavoring agent is selected from the group consisting of fruit flavors.

20. A method of manufacturing a stabilized, essentially sodium free, granular aspirin compound mixed with a granular potassium bicarbonate compound, according to claim 19, wherein said acidic compound is selected from the group consisting of citric acid, maleic acid, tartaric acid, ascorbic acid and various mixtures thereof.

\* \* \* \* \*